United States Patent [19]

Effland et al.

[11] Patent Number: 4,812,450

[45] Date of Patent: Mar. 14, 1989

[54] SPIRO((PIPERIDINE-PYRROLIDINE- OR HEXAHYDROAZEPINYL SUBSTITUTED) PYRROLO(2,1-C) (1,4)BENZOXAZEPINES)

[75] Inventors: Richard C. Effland, Bridgewater; Larry Davis, Sergeantsville; Kevin J. Kapples, Little York, all of N.J.

[73] Assignee: Hoechst-Roussel Pharmaceuticals Inc., Somerville, N.J.

[21] Appl. No.: 79,557

[22] Filed: Jul. 30, 1987

[51] Int. Cl.$^4$ .................. C07D 498/22; C07D 403/04; C07D 401/04; A61K 31/555

[52] U.S. Cl. ..................................... 514/211; 540/543; 540/602; 546/198; 546/208; 548/241; 548/518

[58] Field of Search .................. 514/211; 540/543

[56] References Cited

U.S. PATENT DOCUMENTS

| 4,268,515 | 5/1981 | Effland | 424/267 |
| 4,321,385 | 3/1982 | Effland | 546/208 |
| 4,329,464 | 5/1982 | Effland | 546/17 |

OTHER PUBLICATIONS

"Numbering and Indexing of Chemical Substances for Chemical Abstracts", Appendix IV, 1985, pp. 1301–1311.
Davis et al., J. Med. Chem. 26, 1505 (1983).

Primary Examiner—Mark L. Berch
Attorney, Agent, or Firm—Jerome Rosenstock

[57] ABSTRACT

This invention relates to spiro-[(piperidine-, pyrrolidine-, or -hexahyroazepinyl substituted) pyrrolo[2,1-c][1,4]-benzoxazepines] having the following formula

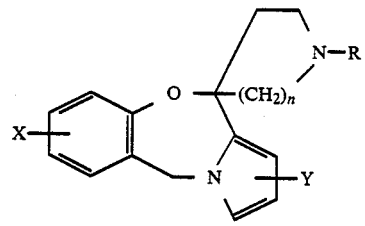

wherein R is hydrogen, lower alkyl, arylloweralkyl, acyl, lower alkenyl, lower alkynyl, and loweralkylbenzisoxazole; X is hydrogen, halogen, loweralkoxy, and trifluoromethyl; Y is hydrogen; 2' or 3' acyl, formyl, carbinol of the formula

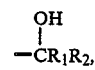

wherein $R_1$ and $R_2$ are the same or different and are independently hydrogen, loweralkyl, arylloweralkyl, aryl, loweralkenyl, lower alkynyl and lower alkylbenzisoxazole; loweralkyl, loweralkenyl and halogen; and n is an integer of 1 to 3. The compounds of this invention display utility as analgesic and antihypertensive agents.

30 Claims, No Drawings

SPIRO((PIPERIDINE-PYRROLIDINE- OR HEXAHYDROAZEPINYL SUBSTITUTED) PYRROLO(2,1-C) (1,4)BENZOXAZEPINES)

This invention relates to compounds of the formula

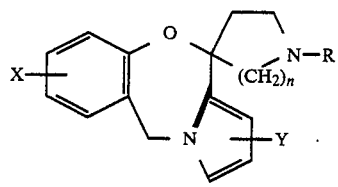

wherein R is hydrogen, loweralkyl, arylloweralkyl, acyl, loweralkenyl, loweralkynyl and loweralkylbenzisoxazole; X is hydrogen, halogen, loweralkoxy and trifluoromethyl; Y is hydrogen, 2' or 3' acyl, formyl; carbinol of the formula

where $R_1$ and $R_2$ are the same or different and are independently hydrogen, loweralkyl, arylloweralkyl, aryl, loweralkenyl, lower alkynyl and lower alkylbenzisoxazole; loweralkyl, lower alkenyl, and halogen; and n is an integer of 1 to 3.

Throughout the specification and appended claims, a given chemical formula or name shall encompass all geometric, optical and stereoisomers thereof where such isomers exist.

In the above definition, the term "lower" means the group it is describing contains from 1 to 6 carbon atoms. The term "alkyl" refers to a straight or branched chain hydrocarbon containing no unsaturation, e.g. methyl, ethyl, isopropyl, 2-butyl, neopentyl, n-hexyl, etc; the term "arylalkyl" refers to a monovalent substituent which consists of an aryl group, e.g. phenyl, o-toluyl, m-methoxyphenyl, etc., of the formula

where Z is as defined below, linked through a loweralkylene group having its free valence bond from a carbon of the loweralkylene group, and having a formula of

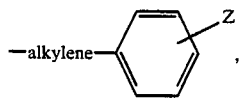

where Z is hydrogen, halogen, loweralkyl, loweralkoxy, $CF_3$, $NO_2$ and $NH_2$; the term "alkylene" refers to a bivalent radical of the lower branched or unbranched alkyl group it is derived from having valence bonds from two terminal carbons thereof, e.g. ethylene (—CH$_2$CH$_2$—), propylene (—CH$_2$CH$_2$CH$_2$—), isopropylene (CH$_3$CH—CH$_2$—), etc; the term "alkoxy" refers to a monovalent substituent which consists of an alkyl group linked through an ether oxygen having its free valence bond from the ether oxygen, e.g. methoxy, ethoxy, propoxy, butoxy, pentoxy, etc; the term "acyl" refers to a substituent having the formula

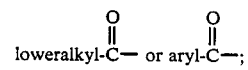

the term "alkenyl" refers to a straight or branched chain hydrocarbon containing one unsaturated carbon to carbon double bond, e.g. $CH_2$=CH—, $CH_3CH$=CH—,

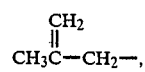

etc.; the term alkynl refers to a straight or branched chain hydrocarbon containing one unsaturated carbon to carbon triple bond, e.g., CH≡C—, $CH_3C$≡C—, etc.; the term loweralkylbenzisoxazole refers to a substituent having the formula,

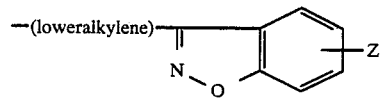

where Z is hydrogen, halogen, loweralkyl, loweralkoxy, $CF_3$, $NO_2$ and $NH_2$; and the term "halogen" refers to a member of the halogen family consisting of fluorine, chlorine, bromine and iodine.

The compounds of the present invention are prepared in the following manner. The substituents R, X and Y are as defined above unless indicated otherwise.

A substituted pyrrole of formula II is selected,

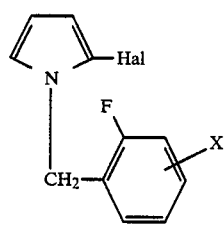

where Hal is a halogen selected from Cl, Br, I. Pyrrole II is reacted under standard selected Grignard reagent forming conditions with magnesium in ether to form a Grignard reagent of the formula III

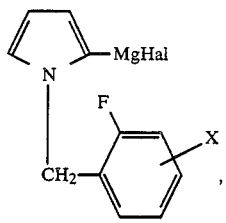

(III)

which in turn is reacted under standard Grignard conditions, such as for example in a non-polar solvent, e.g. tetrahydrofuran, ether, etc., at a temperature of 0° C. to 65° C. for 1 to 3 hours with a ketone of the formula (IV)

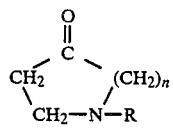

(IV)

to form a tertiary alcohol having the formula

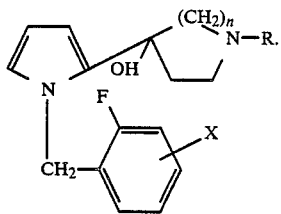

(V)

Alcohol (V) is reacted with a strong base, such as for example sodium hydride, potassium t-butoxide, etc. in a polar solvent, e.g. dimethylformamide, dimethylformamide/benzene mixtures, tetrahydrofurans, etc., typically at a temperature of 25° C. to 100° C. for 1 to 6 hours to achieve intramolecular hydrohalogen displacement to form Compound VI of the formula

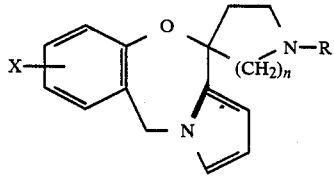

(VI)

[Compound I of the invention, where Y is hydrogen].

Compound VI is reacted with N-halosuccinimide of the formula

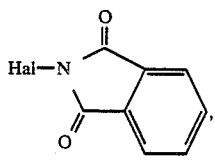

(VII)

where Hal is a halogen selected from Cl, Br, and I, to form Compound VIII

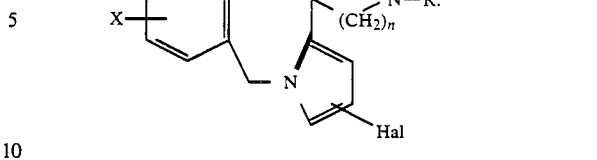

(VIII)

This reaction is typically carried out in a suitable solvent, such as ethereal solvent or a halogenated hydrocarbon, at a temperature of about 0°–60° C.

Compound IX of the invention,

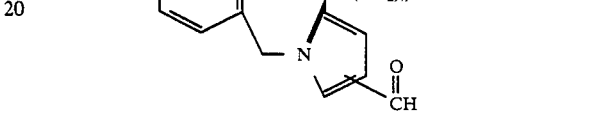

(IX)

is formed by reacting Compound VI with phosphorus oxychloride and dimethyl formamide. This reaction can be conducted under conditions usually employed for carrying out Vilsmeier reactions. Typically, it is conducted in a suitable solvent, such as halogenated hydrocarbon, at a temperature of 20° to 100° C.

Compound IX is subjected to a Wittig reaction with an ylide of the formula

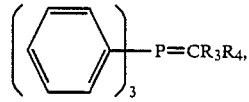

where $R_3$ and $R_4$ are independently hydrogen, loweralkyl, aryl, arylloweralkyl, to form

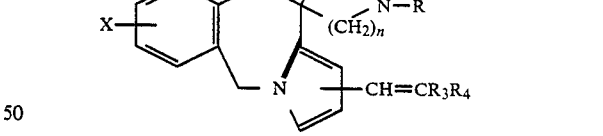

(X)

This reaction is carried out under conditions usually employed for carrying out Wittig reactions. Thus, the ylide is prepared in a routine manner by first preparing a phosphonium salt from a bromide of the formula Br—C($R_3R_4$)H and triphenylphosphine and thereafter reacting the phosphonium salt with a suitable base such as sodium hydride, potassium tert-butoxide or n-butyllithium in a suitable solvent such as anhydrous ethereal solvent. Thereafter a solution of Compound IX in a suitable solvent, such as anhydrous ether, is added to the freshly prepared ylide solution and the mixture is stirred at a temperature of between about −10° C. and 80° C. to form Compound X.

Compound X is catalytically hydrogenated in a suitable manner known to the art to afford a compound of formula XI,

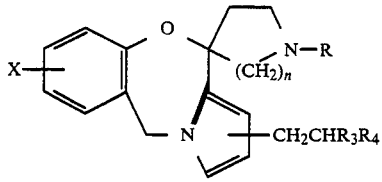
(XI)

Compound VI is reacted with a loweralkanoyl chloride, arylloweralkanoyl chloride or aroylchloride of the formula R₅COCl (XII), where R₅ is loweralkyl, arylloweralkyl or aryl, in the presence of zinc chloride to afford a compound of the formula XIII,

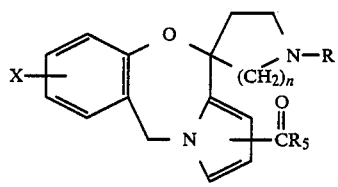
(XIII)

Compound XIII is reacted with a suitable reducing agent, e.g. NaBH₄, LiAlH₄ or borane complexes, to form compound XIV of the formula

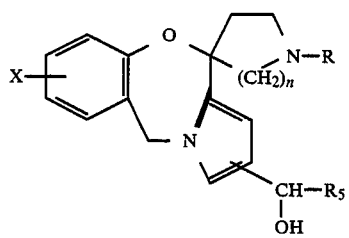
(XIV)

When NaBH₄ is used, the reduction is conducted typically in a lower aliphatic alcohol, such as isopropanol or ethanol, or lower alkanoic acid, at a temperature of about 0° to 80° C. After the reaction, water is added to the reaction mixture. When LiAlH₄ is used, the reduction is conducted typically in an ethereal solvent such as tetrahydrofuran or ether at a temperature of about 0° to 80° C. When borane complexes are used, the reaction temperature is typically 0° to 80° C.

Compound IX is subjected to a Grignard type reaction under conventional Grignard conditions, such as for example in a non-polar solvent, e.g. tetrahydrofuran, ether, etc., at a temperature of 0° to 65° C. for 1 to 3 hours with a Grignard reagent of the formula R₁MgHal (XV), where Hal is halogen selected from Cl, Br and I, to form a carbinol substituted compound of the formula

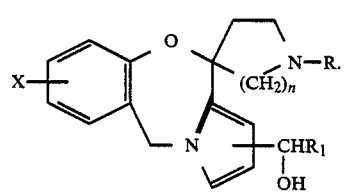
(XVI)

Compound (XIII) is subjected to a similar Grignard reaction to give a carbinol substituted compound of the formula XVI

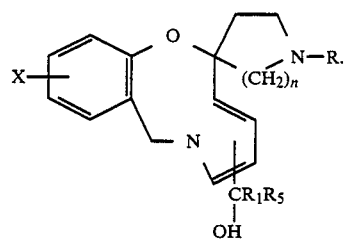
[XVI(a)]

In a preferred embodiment R₁ and R₅ of Compound XVI (a) are lower alkyl.

In an alternative procedure, Compound I, where R is

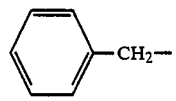

is hydrogenated under pressure in the presence of a noble metal catalyst, e.g. 10% Pd/C, to obtain Compound I where R is hydrogen. Typically this hydrogenation is carried out in a polar solvent, e.g. isopropanol, ethanol, etc., at a temperature of 25° C. to 50° C. for 1 to 20 hours at a pressure of 50 to 30 pounds per square inch.

Compounds of the present invention are useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med. 95, 729 (1957)]. The analgesic activity of some of the compounds expressed in terms of percent inhibitioon of writhing are given in TABLE I.

TABLE I

| Compound | Dose (subcutaneous) (mg/kg of body weight) | Inhibition in Writhing (%) |
|---|---|---|
| 1-Methyl-spiro [piperidine-4,11'(5H)pyrrolo [2,1-c] [1,4] benzoxazepine] | 10.5 | 50 |
| Spiro [piperidine-4,11'(5'H)pyrrolo [2,1-c] [1,4] benzoxazepine] | 5.8 | 50 |
| propoxyphene (standard) | 3.9 | 50 |

The analgesic relief of pain is achieved when the compounds of the invention are administered to a subject requiring such treatment at an effective oral, parenteral or intravenous dose of from 0.1 to 25 mg/kg of body weight per day. A preferred effective dose within this range is from about 1 to 10 mg/kg of body weight per day. A particularly preferred effective amount is about 2 mg/kg of body weight per day. It is to be understood, however, that for any particular subject, specific dosage regimens should be adjusted according to the individual need. It is further to be understood that the dosages set forth herein are examples only and that they do not to any extent, limit the scope of practice of the invention.

The compounds of the present invention are also useful as antihypertensive agents due to their ability to depress blood pressure in mammals. Antihypertensive activity is measured in the spontaneous hypertensive rat by the indirect tail cuff method described in "Methods in Pharmacology," A. Schwartz, Ed., Vol. I, Appleton-Century Crofts, New York, N.Y., 1971, p. 135. In this procedure a group of five animals are treated orally for three days with the test compound in relation to the control group of the same number. The drop in blood pressure is measured on the third day following administration. The antihypertensive activities of some of the compounds, expressed as mm decrease in mean arterial blood pressure are given in Table II.

TABLE II

| Compound | Dose (p.o.) mg/kg of body weight | Decrease in blood pressure mm Hg |
|---|---|---|
| 1-(4-Chlorophenethyl)spiro [piperidine-4,11'(5'H) pyrrolo [2,1-c] [1,4]benzoxazepine | 50 | 32 |
| 1-Butylspiro[piperidine-4,11' (5'H)pyrrolo[2,1-c] [1,4] benzoxazepine maleate | 50 | 23 |
| 1-(2-Phenethyl)spiro[piperidine-4,11'(5'H)pyrrolo[2,1-c] [1,4] benzoxazepine | 50 | 15 |
| 4-[1-(2-Fluorophenyl)methyl-1H—pyrrol-2-yl]-1-(2-phenylethyl)-4-piperidinol | 50 | 27 |
| 2-methyl dopa (reference compound) | 50 | 40 |

Blood pressure reduction is achieved when the compounds of the invention are administered to a subject requiring such treatment at an effective oral, parenteral or intravenous dose of from 0.1 to 50 mg/kg of body weight per day. A preferred effective dose within this range is from about 0.1 to 5 mg/kg of body weight per day. A particularly preferred effective amount is about 1 mg/kg of body weight per day. It is to be understood, however, that for any particular subject, specific dosage regimens should be adjusted according to the individual need and the professional judgment of the person administering or supervising the administration of the compounds of the invention. It is to be further understood that the dosages set forth herein are examples only and that they do not, to any extent, limit the scope or practice of the invention.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% spiro[piperidine-, pyrrolidine-, or hexahydroazepinyl substituted-pyrrolo [2,1-c][1,4]benzoxazepines] of the invention, the active ingredient, but may be varied depending upon the particular form and may conveniently be between 4% to about 70% of the weight of the unit. The amount of the compound present in such compositions is such that a suitable dosage will be obtained. Preferred compositions and preparations according to the present invention are prepared so that an oral dosage unit form contains between 5.0-300 milligrams of the spiro[piperidine-, pyrrolidine-, or hexahydroazepinyl substituted pyrrolo[2,1-c][1,4]benzoxazepines] of the present invention.

The tablets, pills, capsules, troches and the like may also contain the following adjuvants: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of the spiro[piperidine-, pyrrolidine- or hexahydroazepinyl substituted-pyrrolo[2,1-c][1,4]benzoxazepine] derivative of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the spiro[piperidine-, pyrrolidine- or hexahydroazepinyl substituted-pyrrolo[2,1-c][1,4]benzoxazepine] derivative of the invention.

The solutions or suspensions may also include the following adjuvants: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of some of the compounds include:
1-acetylspiro[piperidine-4,11'(5'H)-pyrrolo[2,1-c][1,4]benzoxazepine];
1-oxobutylspiro[piperidine-4,11'(5'H)pyrrolo[2,1-c][1,4]benzoxazepine];
1-(3-butenyl)spiro[piperidine-4,11'(5'H)pyrrolo[2,1-c][1,4]benzoxazepine];
1-(3-methyl-2-butenyl)spiro[piperidine-4,11'(5'H)pyrrolo[2,1-c][1,4]benzoxazepine];
1-(2-propynyl)spiro[piperidine-4,11'(5'H)pyrrolo[2,1-c][1,4]benzoxazepine];
1-cyclopropylmethylspiro[piperidine-4,11(5'H)pyrrolo[2,1-c][1,4]benzoxazepine];

6'-fluorospiro[piperidine-4,11'(5'H)pyrrolo[2,1-c][1,4]benzoxazepine];
8'-chlorospiro[piperidine-4,11'(5'H)pyrrolo[2,1-c][1,4]benzoxazepine];
8'-(1-ethyl-propoxy)spiro[piperidine-4,11'(5'H)pyrrolo[2,1-c][1,4]benzoxazepine];
8'-trifluoromethylspiro[piperidine-4,11'(5'H)pyrrolo[2,1-c][1,4]benzoxazepine];
1-(2-methyl-oxopropyl)spiro[piperidine-4,11'(5'H)pyrrolo[2,1-c][1,4]benzoxazepine];
3'-formylspiro[piperidine-4,11'(5'H)pyrrolo[2,1-c][1,4]benzoxazepine];
2'-pentylspiro[piperidine-4,11'(5'H)pyrrolo[2,1-c][1,4]benzoxazepine];
3'-bromospiro[piperidine-4,11'(5'H)pyrrolo[2,1-c][1,4]benzoxazepine];
3'-(1-butenyl)spiro[piperidine-4,11'(5'H)pyrrolo[2,1-c][1,4]benzoxazepine];
2'-(1-propenyl)spiro[piperidine-4,11'(5'H)pyrrolo[2,1-c][1,4]benzoxazepine];
7'-fluoro-1-propylspiro[piperidine-4,11'(5'H)pyrrolo[2,1-c][1,4]benzoxazepine];
0  7'-ethoxy-1-(4,-diphenylbutyl)spiro[piperidine-4,11'(5'H)pyrrolo[2,1-c][1,4]benzoxazepine];
1-acetyl-6'-trifluoromethylspiro[piperidine-4,11'(5'H)pyrrolo[2,1-c][1,4]benzoxazepine];
9'-chloro-1-(2-propenyl)spiro[piperidine-4,11'(5'H)pyrrolo[2,1-c][1,4]benzoxazepine];
6'-methoxy-1-(2-propynyl)spiro[piperidine-4,11(5'H)pyrrolo[2,1-c][1,4]benzoxazepine];
3'-acetyl-1-methylspiro[piperidine-4,11'(5'H)pyrrolo[2,1-c][1,4]benzoxazepine];
3'-formyl-1-phenbutylspiro[piperidine-4,11'(5'H)pyrrolo[2,1-c][1,4]benzoxazepine];
3'-oxopropyl-1-[(3-methyl)butyl]spiro[piperidine-4,11'(5'H)pyrrolo-4,11'(5'H)pyrrolo[2,1-c][1,4]benzoxazepine];
1-ethyl-3'ethenylspiro[piperidine-4,11'(5'H)pyrrolo[2,1-c][1,4]benzoxazepine];
2'-iodo-1-methylspiro[piperidine-4,11'(5'H)pyrrolo[2,1-c][1,4]benzoxazepine];
3'-acetyl-8'-fluorospiro[piperidine-4,11'(5'H)pyrrolo[2,1-c]1,4]benzoxazepine];
3'-formyl-6'-methoxy-1-methylspiro[piperidine-4,11'(5'H)pyrrolo2.1-c][1,4]benzoxazepine];
3'-propyl-9'-trifluoromethylspiro[piperidine-4,11'(5'H)pyrrolo[2,1-c][1,4]benzoxazepine];
7'-chloro-2'-(1-propenyl)spiro[piperidine-4,11'(5'H)pyrrolo[2,1-c][1,4]benzoxazepine];
3'-bromo-6'-chlorospiro-[piperidine-4,11'(5'H)pyrrolo2,1-c][1,4]benzoxazepine];
3'-acetyl-9'-fluoro-1-methylspiro[piperidine-4,11'(5'H)pyrrolo2,1-c][1,4]benzoxazepine];
8'-chloro-2'-formyl-1-phenylmethylspiro[piperidine-4,11(5'H)pyrrolo[2,1-c][1,4]benzoxazepine];
1-acetyl-8'-methoxy-3'propylspiro[piperidine-4,11'(5'H)pyrrolo2,1-c][1,4]benzoxazepine];
3'-ethenyl-1-(2-propenyl)-6'-trifluoromethylspiro[-piperidine-4,11'(5'H)pyrrolo[2,1-c][1,4]benzoxazepine];
8'-butoxy-2'-iodo-1-(butyl)spiro[piperidine-4,11'(5'H)pyrrolo[2,1-c][1,4]benzoxazepine];
1-methyl-spiro[pyrrolidine-3,11'(5'H)pyrrolo[2,1c][1,4-]benzoxazepine];
spiro[pyrrolidine-3,11'(5'H)pyrrolo[2,1-c][1,4]benzoxazepine];
1-benzyl-spiro[pyrrolidine-3,11'(5'H)pyrrolo[2,1-c]1,4]benzoxazepine];
1-phenylethyl-spiro[pyrrolidine-3,11'(5'H)pyrrolo[2,1-c]1,4]benzoxazepine];
3'-chloro-1-methyl-spiro[pyrrolidine-3,11'(5'H)pyrrolo2,1-c][1,4]benzoxazepine];
3'-chloro-spiro[pyrrolidine-3,11'(5'H)pyrrolo[2,1-c][1,4]benzoxazepine];
3'-chloro-8'-fluoro-1-methyl-spiro[pyrrolidine-3,11'(5'H)pyrrolo[2,1-c][1,4]benzoxazepine];
8'-fluoro-spiro[pyrrolidine-3,11'(5'H)pyrrolo[2,1-c][1,4]benzoxazepine];
1-benzyl-7'-methoxy-spiro[pyrrolidine-3,11'(5'H)pyrrolo2,1-c][1,4]benzoxazepine];
methyl-spiro[2,3,4,5,6,7-hexahydro-1H-azepine-4,11'(5'H)pyrrolo[2,1-c][1,4]benzoxazepine];
spiro[2,3,4,5,6,7-hexahydro-1H-azepine-4,11'(5'H)pyrrolo2,1-c][1,4]benzoxazepine];
1-benzyl-spiro[2,3,4,5,6,7-hexahydro-1H-azepine-4,11'(5'H)pyrrolo2,1-c][1,4]benzoxazepine];
1-phenylethyl-spiro[2,3,4,5,6,7-hexahydro-1H-azepine-4,11'(5'H)pyrrolo[2,1-c][1,4]benzoxazepine];
3'-chloro-1-methyl-spiro[2,3,4,5,6,7-hexahydro-1H-azepine-4,11'(5'H)pyrrolo[2,1-c][1,4]benzoxazepine];
3'-bromo-spiro[2,3,4,5,6,7-hexahydro-1H-azepine-4,11'(5'H)pyrrolo[2,1-c][1,4]benzoxazepine];
3'-chloro-8'-fluoro-1-phenylethyl-spiro[2,3,4,5,6,7-hexahydro-1H- azepine-4,11'(5'H)pyrrolo[2,1-c][1,4]benzoxazepine];
8'-fluoro-spiro[2,3,4,5,6,7-hexahydro-1H-azepine-4,11'(5'H)pyrrolo[2,1-c[1,4]benzoxazepine].

The following examples are for illustrative purposes and are not to be construed as limiting the invention disclosed herein. All temperatures are given in degrees centigrade.

EXAMPLE 1 a.

4-[1-(2-Fluorophenyl)methyl-1H-pyrrol-2-yl]-1-(2-phenylethyl)-4-piperidinol

A solution of 2-bromo-1-[(2-fluorophenyl)methyl]-pyrrole (11.18 g; 0.044 moles in 30 ml tetrahydrofuran [THF]) was added to a suspension of magnesium turnings (1.17 g; 0.048 moles in 40 ml 10% ether/THF). The reaction mixture was initiated with a few drops of 1,2-dibromoethane and heat and was then refluxed for 30 minutes. To this mixture was added a solution of 1-(2-phenylethyl)-4-piperidone (7.73 g; 0.038 moles in 40 ml THF). The reaction was then refluxed for 45 minutes. The reaction was quenched into iced NH$_4$Cl solution and this was extracted thrice with ethyl acetate. The combined organics were washed once with water and dried (saturated NaCl solution, anhydrous MgSO$_4$). The solution was filtered and concentrated to a semisolid product which was then purified via high pressure liquid chromatography (HPLC) [THF:dichloromethane:diethylamine/10:90:0.5] to give 7.26 g (50%) of a solid, m.p. 125°–129° C. The solid was recrystallized from isopropyl ether to give 4-[1-(2-fluorophenyl)methyl-1H-pyrrol-2-yl]-1-(2-phenylethyl)-4-piperidinol, m.p. 130°–131° C.

Analysis:
Calculated for $C_{24}H_{27}FN_2O$: 76.16% C, 7.19% H, 7.40% N.
Found: 76.02% C, 7.23% H, 7.37% N.

b.
1-(2-Phenylethyl)spiro[piperidine-4,11'(5'H)pyrrolo[2,1-c][1,4]benzoxazepine]

To a suspension of NaH (0.66 g; 0.014 moles 50% in oil, treated with hexane) in 15 ml 20% dimethylformamide (DMF)/benzene was added a solution of 4-[1-(2-fluorophenyl)methyl-1H-pyrrol-2-yl]-1-(2-phenylethyl)-4-piperidinol of Example 1a. (4.33 g; 0.011 moles in 85 ml 20% DMF/benzene). This was heated at 70° C. for 3.5 hours. The reaction was then quenched into iced H$_2$O and extracted thrice with ethyl acetate. The combined organics were washed once with H$_2$O and dried (saturated NaCl solution, anhydrous MgSO$_4$). The resultant solution was filtered and concentrated to an oil which was purified via HPLC (2% methanol/dichloromethane) to yield 3.26 g (83%) of a solid, m.p.:slight melt at 70°-73° C., 150°-152° C. The solid was recrystallized from isopropyl ether to give 1-(2-phenylethyl)spiro[piperidine-4,11'(5'H)pyrrolo[2,1-c][1,4]benzoxazepine], m.p. initial:73.5°-75° C., final, 150°-152° C.

Analysis: Calculated for C$_{24}$H$_{26}$N$_2$O: 80.41% C, 7.31% H, 7.81% N.

Found: 80.25% C, 7.35% H, 7.69% N.

EXAMPLE 2 a.
4-[1-(2-Fluorophenyl)methyl-1H-pyrrol-2-yl]-1-methyl-4-piperidinol

A solution of 2-bromo-1-[(2-fluorophenyl)methyl]-pyrrole(11.9 g; 0.047 moles in 25 ml THF) was added to a suspension of magnesium turnings (1.3 g; 0.05 moles in 20 ml THF/5 ml ether). The reaction was initiated with a few drops of 1,2-dibromoethane and a reflux was maintained by addition of the pyrrole. After the reflux subsided, the reaction was cooled to ice bath temperature. To this was added a solution of 1-methyl-4-piperidone (3.5 g; 0.03 moles in 15 ml THF). The reaction was stirred for 20 minutes and quenched into iced NH$_4$Cl solution. This was extracted twice with ethyl acetate and the combined organics were washed once with H$_2$O and dried (saturated NaCl solution, anhydrous MgSO$_4$). The resultant solution was filtered and concentrated to give a semi-solid. Trituration of this material with hexane yielded 3.22 g (36%) of a solid, m.p. 159°-162° C. This solid was recrystallized from isopropyl ether to give 4-[1-(2-fluorophenyl)methyl-1H-pyrrol-2-yl]-1-methyl-4-piperidinol, m.p. 164°-165° C.

Analysis Calculated for C$_{17}$H$_{21}$FN$_2$O: 70.81% C, 7.34% H, 9.71% H.

Found: 70.64% C, 7.41% H, 9.56% H.

b.
1-Methylspiro[piperidine-4,11'(5'H)pyrrolo[2,1-c][1,4]benzoxazepine

To a suspension of sodium hydride (0.7 g; 0.014 moles, 50% in oil, treated with hexane) in 30 ml 20% DMF/benzene was added a solution of 4-[1-(2-fluorophenyl)methyl-1H-pyrrol-2-yl]-1-methyl-4-piperidinol of Example 2a, (3,2 g; 0.011 moles) in 30 ml 20% DMF/benzene. This was heated at 70° C. oil bath temperature for four hours. The reaction was then quenched into dilute NaCl solution and extracted twice with diethyl ether. The combined organics were washed once with H$_2$O and dried (saturated NaCl solution, anhydrous MgSO$_4$). This was filtered and concentrated to give a semi-solid. This solid was purified via HPLC (3% methanol/dichloromethane) to yield 1.85 g (63%) of a solid, m.p. 94°-100° C. The solid was recrystallized from isopropyl ether to give 1-methyl-spiro[piperidine-4,11'(5'H)pyrrolo[2,1-c][1,4]benzoxazepine], m.p. 100°-101° C.

Analysis: Calculated for C$_{17}$H$_{20}$N$_2$O: 76.09% C, 7.51% H, 10.44% N.

Found: 75.84% C, 7.45% H, 10.30% N.

EXAMPLE 3 a.
1-(4-Chlorophenethyl)-4-[1-(2-fluorobenzyl)pyrrol-2-yl]-4-piperidinol

To a suspension of magnesium turnings (1.0 g, 0.04 mole) in 25 ml tetrahydrofuran (THF) and 10 ml ether, was added a few drops of a solution of 2-bromo-1-(2-fluorobenzyl) pyrrole (10.0 g, 0.04 mole) in 30 ml THF. The reaction was initiated with a few drops of dibromoethane and heat, and reflux was maintained by the addition of the bromo compound after stirring at reflux for 30 minutes, the mixture was cooled with an ice-bath; then a solution of 1-(4-chlorophenethyl)-4-piperidone (5.0 g, 0.021 mole) was added. After stirring at ambient temperature for one hour, the mixture was poured into a solution of NH$_4$Cl, then extracted with ether. The ether solution was washed with water, then dried over anhydrous MgSO$_4$. After evaporation of the solvent, the resultant oil, 12 g, was purified by high pressure liquid chromatography (HPLC), using ethyl acetate as the eluent to give 4.5 g of 1-(4-chlorophenethyl)-4-[1-(2-fluorobenzyl)pyrrol-2-yl]-4-piperidinol, m.p. 108°-9° C.

b.
1-(4-Chlorophenethyl)spiro[piperidine-4,11'(5'H)pyrrolo[2,1-c][1,4]benzoxazepine]

To a suspension of NaH (50% in oil, washed with hexanes, 0.62 g, 0.013 mole) in 20 ml benzene, was added a solution of 1-(4-chlorophenethyl)-4-[1-(2-fluorobenzyl)pyrrol-2-yl]-4-piperidinol (4.0 g, 0.01 mole) of Example 3a in 50 ml benzene and 30mml DMF. After stirring at 90° C. for two hours, the mixture was poured into 200 ml water and stirred for five minutes, then extracted with ethyl acetate/ether. The organic layer was washed twice with water, then dried (saturated NaCl, anhydrous MgSO$_4$). After filtering, the solvents were evaporated to a solid, 3.6 g, m.p. 105°-108° C., which was recrystallized from isopropyl ether to yield 3.0 g (75%) of product, m.p. 114°-5° C. This material was recrystallized from isopropyl ether to give 2.5 g of 1-(4-chlorophenethyl)spiro[piperidine-4,11'(5'H)pyrrolo[2,1-c][1,4]benzoxazepine], m.p. 116°-8° C.

Analysis: Calculated for C$_{24}$H$_{25}$ClN$_2$O: 73.36% C, 6.41% H, 7.13% N.

Found: 73.28% C, 6.54% H, 6.96% N.

EXAMPLE 4 a.
4-[1-(2-Fluorophenyl)methyl-1H-pyrrol-2-yl]-1-benzyl-4-piperidinol

To a suspension of magnesium turnings (2.2 g, 0.09 mole) in 60 ml tetrahydrofuran (THF) and 30 ml ether, was added a few drops of a solution of 2-bromo-1-(2-fluorobenzyl)pyrrole (20 g, 0.074 mole) in 60 ml THF. The reaction was initiated with a few drops of dibromoethane and heat, and reflux was maintained by the addition of the bromo compound. After stirring at reflux for 30 minutes, the mixture was cooled with an ice bath, then a solution of 1-benzyl-4-piperidone (11.2 g, 0.06 mole) in 75 ml THF was added. After stirring at ambient temperature for one hour, the mixture was poured into $NH_4Cl$ solution, then extracted with ethyl acetate. The ethyl acetate solution was washed with water, then dried over anhydrous $MgSO_4$. After evaporation of the solvent, the resultant oil (25 g) was purified by HPLC, using ethyl acetate/hexane/diethylamine (30:70:0.5) as the eluent to give 15.8 g of 4-[1-((2-fluorophenyl)methyl)-1H-pyrrol-2-yl]-1-benzyl-4-piperidinol, m.p. 112°–117° C.

b.
1-Benzylspiro[piperidine-4,11'(5'H)pyrrolo[2,1-c][1,4]benzoxazepine]

To a suspension of sodium hydride (2.55 g; 0.052 moles; 50% in oil, treated with hexane) in 30 ml 30% DMF/benzene was added a solution of 4-[1-(2-fluorophenyl)methyl-1H-pyrrol-2-yl]-1-benzyl-4-piperidinol (14.5 g; 0.014 moles) in 120 ml 30% DMF/benzene of Example 4a. This mixture was heated at 75° C. for 4.5 hours. The mixture was quenched into iced $H_2O$ and extracted twice with ethyl acetate. The combined organics were washed twice with $H_2O$ and dried (saturated NaCl solution, anhydrous $MgSO_4$). This was filtered and concentrated to an oil. The amine product was crystallized out by treating the oil with isopropyl ether to give 8.55 g (61%) of a solid, m.p. 105°–109° C. This solid was twice recrystallized from isopropyl ether to give 1-benzylspiro[piperidine-4,11'(5'H)pyrrolo[2,1-c][1,4]benzoxazepine], m.p. 109°–111° C.
analysis:
Calculated for $C_{23}H_{24}N_2O$: 80.20% C, 7.02% H, 8.13% N. Found: 80.59% C, 7.06% H, 7.56% N.

EXAMPLE 5

Spiro[piperidine-4,11'(5'H)pyrrolo[2,1-c][1,4]benzoxazepine]maleate

A suspension of 1-benzylspiro[piperidine-4,11'-(5'H)pyrrolo[2,1-c][1,4]benzoxazepine](4.8 g; 0.014 moles) of Example 4b and 1.5 g 10% Pd/C in 150 ml isopropanol in a Parr hydrogenation apparatus, was pressurized to 50 psi with hydrogen and heated to 50° C. The mixture was shaken for eight hours and let stand under hydrogen overnight. The catalyst was then filtered and the solution concentrated to give an oil. The resultant amine was purified via HPLC (THF:diethylamine; 100:1) to yield 2.9 g (81%) of a semi-solid. The maleate salt of the amine was formed via addition of a maleic acid/diethyl ether solution to give 3.05 g of a solid, m.p. 167°–170° C. The solid was recrystallized three times from isopropanol/diethyl ether (1:2) to give spiro[piperidine-4,11'(5'H)pyrrolo[2,1-c][1,4]benzoxazepine]. m.p. 168°–170° C.
Analysis: Calculated for $C_{16}H_{18}N_2O.C_4H_4O_4$: 64.85%C, 5.99% H, 7.56% N. Found: 64.70% C, 6.21% H, 7.47% N.

EXAMPLE 6 a.
1-Butyl-4-[1-(2-fluorobenzyl)pyrrol-2-yl]-4-piperidinol

To a suspension of magnesium turnings (1.0 g, 0.04 mole) in 25 ml tetrahydrofuran (THF) and 10 ml ether, was added a few drops of a solution of 2-bromo-1-(2-fluorobenzyl)pyrrole (10 g, 0.04 mole) in 35 ml THF. The reaction was initiated with a few drops of dibromoethane and heat, and reflux was maintained by the addition of the bromo compound. After stirring at reflux for thirty minutes, the mixture was cooled with an ice-bath, then a solution of 1-butyl-4-piperidone (4.6 g, 0.03 mole) in 25 ml THF was added. After stirring at ambient temperature for one hour, the mixture was poured into an $NH_4Cl$ solution, then extracted with ether. The ether solution was washed with water, then dried over anhydrous $MgSO_4$. After evaporation of the solvent, the resultant oil (11 g) was purified by HPLC using ethyl acetate as the eluent to give 3.4 g of 1-butyl-4-[1-(2-fluorobenzyl)pyrrol-2-yl]-4-piperidinol; m.p. 132°–5° C.

b.
1-Butylspiro[piperidine-4,11'(5'H)pyrrolo[2,1-c][1,4]benzoxazepine]maleate

To a suspension of NaH (50% in oil, washed with hexanes, 0.62 g, 0.013 mole) in 20 ml benzene, was added a solution of 1-butyl-4-[1-(2-fluorobenzyl)pyrrol-2-yl]-4-piperidinol (3.2 g, 0.01 mole) of Example 6a in 50 ml benzene and 30 ml DMF. After stirring at 90° C. for seven hours, the mixture was poured into 200 ml water, stirred for five minutes, then extracted with ether. The organic layer was washed twice with water, then dried (saturated NaCl, anhydrous $MgSO_4$). After filtering, the solvents were evaporated to an oil, (3 g), which was dissolved in ether, then acidified to pH 1 with ethereal maleic acid. The resultant precipitate was collected and dried to yield 2.7 g (64%) of product, m.p. 163°–166° C. This compound was recrystallized twice from isopropanol/ether (1:10) to yield 1-butyl-spiro[piperidine-4,11'(5'H)pyrrolo[2,1-c][1,4]benzoxazepine]maleate, m.p. 175°–7° C.
Analysis:
Calculated for $C_{20}H_{26}N_2O.C_4H_4O_4$: 67.58% C, 7.09% H, 6.57% N. Found: 67.40% C, 7.00% H, 6.55% N.

EXAMPLE 7 a.
1-[3-(6-Fluoro-1,2-benzisoxazol-3-yl)propyl]-4-[1-(2-fluorobenzyl)pyrrol-2-yl]-4-piperidinol To a suspension of magnesium turnings (1.0 g, 0.04 mole) in 25 ml tetrahydrofuran (THF) and 10 ml ether, was added a few drops of a solution of 2-bromo-1-(2-fluorobenzyl)pyrrole (10 g, 0.04 mole) in 30 ml THF. The reaction was initiated with a few drops of dibromoethane and heat, and reflux was maintained by the addition of the bromo compound. After stirring at reflux for 30 minutes, the mixture was cooled; then a solution of 1-[3-(6-fluoro-1,2-benzisoxazol-3-yl)propyl]-4-piperidone (5.2 g, 0.019 mole) in 50 ml THF was added. After stirring at ambient temperature for one hour, the mixture was poured into an $NH_4Cl$ solution, then extracted with ether. The ether layer was washed with water, then dried over anhydrous $MgSO_4$. After evaporation of the solvent, the resultant oil (13 g), was purified by HPLC using ethyl acetate with 0.5% Diethylamine as the eluent to give 6.2 g of 1-[3-(6-fluoro-1,2-benzisoxazol-3-yl)propyl]-4-[1-(2-fluorobenzyl)pyrrol-2-yl]-4-piperidinol, m.p. 100°–4° C.

b. 1-[3-(6-Fluoro-1,2-benzisoxazol-3-yl)propyl]spiro[piperidine-4,11′(5′H)-pyrrolo[2,1-c][1,4]benzoxazepine]maleate To 80 ml benzene and 20 ml DMF was added sodium hydride (0.72 g, 0.015 mole, 50% in oil, treated with hexanes) and 1-[3-(6-fluoro-1,2-benzisoxazol-3-yl)propyl]-4-[1-(2-fluorobenzyl)pyrrol-2-yl]-4-piperidinol (5.2 g, 0.012 mole) of Example 7a. After stirring at 80° C. for five hours, the mixture was poured into 500 ml water, stirred for five minutes, then extracted with ether/ethyl acetate. The organic layer was collected, washed twice with water, then dried (saturated NaCl, anhydrous MgSO4). After filtering, the solvents were evaporated to an oil, which was dissolved in ether, then acidified to pH 1 with ethereal-maleic acid. The resultant precipitate was collected and dried to yield 5.5 (84%), of product, m.p. 155° C. This compound was recrystallized twice from isopropanol/methanol/ether (5:1:5) to yield 1-[3-(6-fluoro-1,2-benzisoxazol-3-3-yl)propyl]spiro[piperidine-4,11′(5′H)pyrrolo[2,1-c][1,4]benzoxazepine]maleate, m.p. 163°–165° C.

Analysis:
Calculated for $C_{26}H_{26}FN_3O_2 \cdot C_4H_4O_4$: 65.80% C, 5.52% H, 7.67% N. Found: 66.20% C, 5.79% H, 7.72% N.

We claim:

1. A spiro(piperidine-, pyrrolidine- or hexahydroazepine)pyrrolo[2,1a][1,4]benzoxazepine of the formula

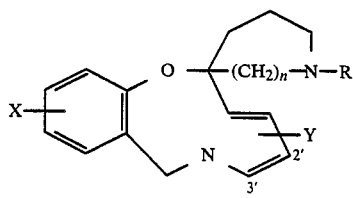

wherein R is hydrogen, loweralkyl, arylloweralkyl, acyl, loweralkynyl, loweralkynyl and

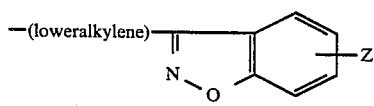

where Z is hydrogen, halogen, loweralkyl, loweralkoxy, $CF_3$, $NO_2$ and $NH_2$; X is hydrogen, halogen, loweralkoxy and trifluoromethyl; Y is hydrogen, 2′ or 3′ acyl, formyl, carbinol of the formula

where $R_1$ and $R_2$ are the same or different and are independently hydrogen, loweralkyl, arylloweralkyl, aryl, lower alkenyl, lower alkynyl and lower alkylbenzisoxazole; loweralkyl, loweralkenyl and halogen; and n is an integer of from 1 to 3 and the pharmaceutically acceptable acid addition salts thereof and where applicable to the geometric and stereo isomers thereof.

2. The compound as defined in claim 1 wherein n is 1.

3. The compound as defined in claim 1 wherein n is 2.

4. The compound as defined in claim 3 which is 1-(2-phenylethyl)spiro[piperidine-4,11′(5′H)pyrrolo[2,1-c][1,4]benzoxazepine] and the pharmaceutically acceptable addition salts thereof.

5. The compound as defined in claim 3 which is 1-methylspiro[piperidine-4,11′(5′H)pyrrolo[2,1-c][1,4]benzoxazepine] and the pharmaceutically acceptable addition salts thereof.

6. The compound as defined in claim 3 which is 1-(4-chlorophenethyl)spiro [piperidine-4,11′(5′H)pyrrolo[2,1-c][1,4]benzoxazepine] and the pharmaceutically acceptable addition salts thereof.

7. The compound as defined in claim 3 which is 1-benzylspiro[piperidine-4,11′(5′H)pyrrolo[2,1-c][1,4]benzoxazepine] and the pharmaceutically acceptable addition salts thereof.

8. The compound as defined in claim 3 which is spiro[piperidine-4,11′(5′H)pyrrolo[2,1-c][1,4]benzoxazepine] and the pharmaceutically acceptable addition salts thereof.

9. The compound as defined in claim 3 which is 1-butylspiro [piperidine-4,11′(5′H)pyrrolo[2,1-c][1,4]benzoxazepine] and the pharmaceutically acceptable addition salts thereof.

10. The compound as defined in claim 3 which is 1-[3-(6-fluoro-1,2-benzisoxazol-3-yl)propyl]spiro[piperidine-4,11′(5′H)pyrrolo[2,1-c][1,4]benzoxazepine] and the pharmaceutically acceptable addition salts thereof.

11. An analgesic composition which comprises an effective pain alleviating amount of a compound of the formula

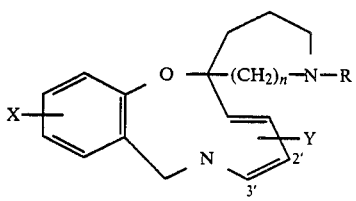

wherein R is hydrogen, loweralkyl, arylloweralkyl, acyl, loweralkenyl, loweralkynyl, and

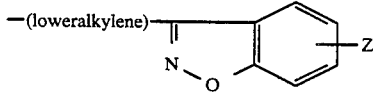

where Z is hydrogen, halogen, loweralkyl, loweralkoxy, $CF_3$, $NO_2$ and $NH_2$; X is hydrogen, halogen, loweralkoxy and trifluoromethyl; Y is hydrogen, 2′ or 3′ acyl, formyl, carbinol of the formula

where $R_1$ and $R_2$ are the same or different and are independently hydrogen, loweralkyl, arylloweralkyl, aryl, lower alkenyl, lower alkynyl and lower alkylbenzisoxazole; loweralkyl, loweralkenyl and halogen; and n is an integer of from 1 to 3 and the pharmaceutically acceptable acid addition salts thereof and where applicable to the geometric, stereo and optical isomers thereof; and a suitable carrier therefor.

12. The composition as defined in claim 11 wherein n is 1.

13. The composition as defined in claim 11 wherein n is 2.

14. The composition as defined in claim 13 which comprises 1-(2-phenylethyl)spiro[piperidine-4,11′(5′H)pyrrolo[2,1-c][1,4]benzoxazepine] and the pharmaceutically acceptable addition salts thereof.

15. The composition as defined in claim 13 which comprises 1-methylspiro[piperidine-4,11′(5′H)pyrrolo[2,1-c][1,4]benzoxazepine] and the pharmaceutically acceptable addition salts thereof.

16. The composition as defined in claim 13 which comprises 1-(4-chlorophenethyl)spiro[piperidine-4,11′(5′H)pyrrolo[2,1-c][1,4]benzoxazepine] and the pharmaceutically acceptable addition salts thereof.

17. The composition as defined in claim 13 which comprises 1-benzylspiro[piperidine-4,11′(5′H)pyrrolo[2,1-c][1,4]benzoxazepine] and the pharmaceutically acceptable addition salts thereof.

18. The composition as defined in claim 13 which comprises spiro[piperidine-4,11′(5′H)pyrrolo[2,1-c][1,4]benzoxazepine] and the pharmaceutically acceptable addition salts thereof.

19. The composition as defined in claim 13 which comprises 1-butylspiro[piperidine-4,11′(5′H)pyrrolo[2,1-c][1,4]benzoxazepine] and the pharmaceutically acceptable addition salts thereof.

20. The composition as defined in claim 13 which comprises 1-[3-(6-fluoro-1,2-benzisoxazol-3-yl)propyl]spiro[piperidine-4,11′(5′H)pyrrolo[2,1-c][1,4]benzoxazepine] and the pharmaceutically acceptable addition salts thereof.

21. A method of alleviating pain in a mammal which comprises administering to a mammal a pain alleviating effective amount of a compound of the formula

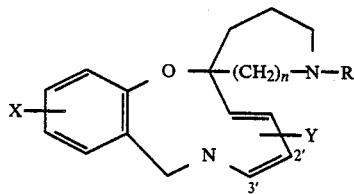

wherein R is hydrogen, loweralkyl, arylloweralkyl, acyl, loweralkenyl, loweralkynyl, and

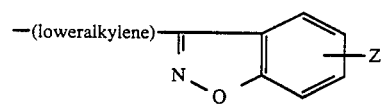

where Z is hydrogen, halogen, loweralkyl, loweralkoxy, $CF_3$, $NO_2$ and $NH_2$; X is hydrogen, halogen, loweralkoxy and trifluoromethyl; Y is hydrogen, 2′ or 3′ acyl, formyl, carbinol of the formula $$\begin{array}{c} OH \\ | \\ -CR_1R_2, \end{array}$$

where $R_1$, and $R_2$ are the same or different and are independently hydrogen, loweralkyl, arylloweralkyl, aryl, loweralkenyl, loweralkynyl, and lower alkylbenzisoxazole; loweralkyl, loweralkenyl, and halogen; and n is an integer of from 1 to 3 and the pharmaceutically acceptable acid addition salts thereof and where applicable to the geometric, stereo and optical isomers thereof.

22. The method as defined in claim 21 wherein n is 1.

23. The method as defined in claim 21 wherein n is 2.

24. The method as defined in claim 23 wherein said compound is 1-(2-phenylethyl)spiro[piperidine-4,11′(5′H)pyrrolo[2,1-c][1,4]benzoxazepine] and the pharmaceutically acceptable addition salts thereof.

25. The method as defined in claim 23 wherein said compound is 1-methylspiro[piperidine-4,11′(5′H)pyrrolo[2,1-c][1,4]benzoxazepine] and the pharmaceutically acceptable addition salts thereof.

26. The method as defined in claim 23 wherein said compound is 1-(4-chlorophenethyl)spiro[piperidine-4,11′(5′H)pyrrolo[2,1-c][1,4]benzoxazepine] and the pharmaceutically acceptable addition salts thereof.

27. The method as defined in claim 23 wherein said compound is 1-benzylspiro[piperidine-4,11′(5′H)pyrrolo[2,1-c][1,4]benzoxazepine] and the pharmaceutically acceptable addition salts thereof.

28. The method as defined in claim 23 wherein said compound is spiro[piperidine-4,11′(5′H)pyrrolo[2,1-c][1,4]benzoxazepine] and the pharmaceutically acceptable addition salts thereof.

29. The method as defined in claim 23 wherein said compound is 1-butylspiro[piperidine-4,11′(5′H)pyrrolo[2,1-c][1,4]benzoxazepine] and the pharmaceutically acceptable addition salts thereof.

30. The method as defined in claim 23 wherein said compound is 1-[3-(6-fluoro-1,2-benzisoxazol-3-yl)propyl]spiro[piperidine-4,11′(5′H)pyrrolo[2,1-c][1,4]benzoxazepine] and the pharmaceutically acceptable addition salts thereof.

* * * * *

UNITED STATES PATENT AND TRADEMARK OFFICE
CERTIFICATE OF CORRECTION

PATENT NO. : 4,812,450

DATED : March 14, 1989

INVENTOR(S) : Richard C. Effland, et al.

It is certified that error appears in the above-identified patent and that said Letters Patent is hereby corrected as shown below:

Claim 1, line 35, the first structure

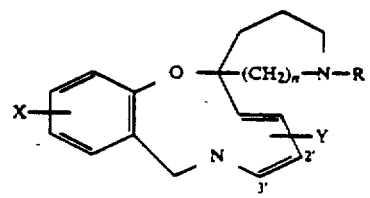

should read

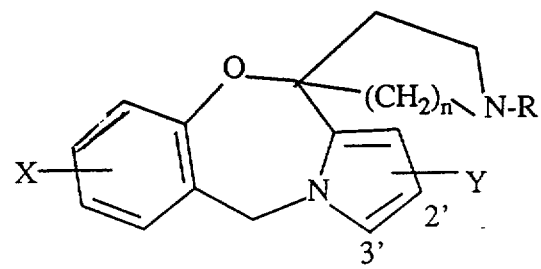

UNITED STATES PATENT AND TRADEMARK OFFICE
CERTIFICATE OF CORRECTION

PATENT NO. : 4,812,450

DATED : March 14, 1989

INVENTOR(S) : Richard C. Effland, et al.

It is certified that error appears in the above-identified patent and that said Letters Patent is hereby corrected as shown below:

Claim 1, line 45, ...acyl, loweralkynyl, loweralkynyl...
should read         ...acyl, loweralkenyl, loweralkynyl... .

Signed and Sealed this

Seventh Day of August, 1990

Attest:

HARRY F. MANBECK, JR.

*Attesting Officer*    Commissioner of Patents and Trademarks